US005470308A

United States Patent [19]
Edwards et al.

[11] Patent Number: 5,470,308
[45] Date of Patent: Nov. 28, 1995

[54] MEDICAL PROBE WITH BIOPSY STYLET

[75] Inventors: Stuart D. Edwards, Los Altos; Ronald G. Lax, Grass Valley; Hugh R. Sharkey, Redwood City; Ingemar H. Lundquist, Pebble Beach, all of Calif.

[73] Assignee: Vidamed, Inc., Menlo Park, Calif.

[21] Appl. No.: 155,975

[22] Filed: Nov. 19, 1993

Related U.S. Application Data

[63] Continuation-in-part of Ser. No. 929,638, Aug. 12, 1992, abandoned, and Ser. No. 12,370, Feb. 2, 1993, Pat. No. 5,370,675, and Ser. No. 62,364, May 13, 1993, Pat. No. 5,435,805.

[51] Int. Cl.$^6$ ..................................................... A61B 17/39
[52] U.S. Cl. ........................................................... 604/22
[58] Field of Search ............................. 604/22, 164, 280, 604/19–21, 53; 606/1–4, 4–17, 39, 45, 32; 601/2; 607/96, 101, 113, 102, 116, 138, 156

[56] References Cited

U.S. PATENT DOCUMENTS

| | | |
|---|---|---|
| 32,066 | 1/1886 | Leveen . |
| 1,879,249 | 9/1932 | Hansaker ................................. 604/280 |
| 1,950,788 | 3/1934 | Ewerhardt et al. . |
| 1,968,997 | 8/1934 | Drucker . |

(List continued on next page.)

FOREIGN PATENT DOCUMENTS

| | | |
|---|---|---|
| 10858/92 | 8/1992 | Australia . |
| 0370890 | 5/1990 | European Pat. Off. . |
| 0453071 | 10/1991 | European Pat. Off. . |
| 0495443 | 7/1992 | European Pat. Off. . |

(List continued on next page.)

OTHER PUBLICATIONS

Standard Urology Product Catalog, CIRCON ACMI: Stanford (1992).
Chang, Raymond J. et al, American Heart Journal, 125: 1276–1283 (May, 1993).
Cosman, Eric R. et al, Sterostatic and Functional Neurosurgery, pp. 2490–2499 (Date Unknown).
Diasonics, Brochure DIA 2000 171 CRF 5/88.

(List continued on next page.)

*Primary Examiner*—C. Fred Rosenbaum
*Assistant Examiner*—Manuel Mendez
*Attorney, Agent, or Firm*—Flehr, Hohbach, Test, Albritton & Herbert

[57] ABSTRACT

A medical probe apparatus comprising a catheter having a stylet guide housing with at least one stylet port in a side thereof and a stylet guide for directing a flexible stylet outward through at least one stylet port and through intervening tissue to targeted tissues. The stylet guide has a biopsy sample device or other tissue manifesting device at the distal end thereof to gather tissue or perform other operations at the point of the desired tissue such as emitting electromagnetic energy as ablative power to target tissues;.

One embodiment of the biopsy sample stylet includes a hollow core sampler including a biopsy needle apparatus for gathering sample tissue. The hollow core sampler has a sharpened end for facilitating the penetration into and gathering of the sample tissue. A second embodiment of the biopsy sample stylet includes a harpoon-like sample stylet when the sharp tip thereof allows for easy entry into the target tissue. The sharpened barbed side opening allows for certain desired tissue to be sampled to be drawn into the side opening for individual cell gathering or complete sample excise or gathering of the desired tissue. The third embodiment is a clam shell or alligator type biopsy jaw device whereby the sharpened biopsy tip thereof allows a tissue sample to be clipped or cut upon activation of the stylet jaws. Still another embodiment comprises a biopsy knife device in conjunction with an electromagnetic emitter for selective tissue sampling or electromagnetic heat ablation, or both, of selected tissue.

23 Claims, 10 Drawing Sheets

U.S. PATENT DOCUMENTS

| Number | Date | Name | Ref |
|---|---|---|---|
| 2,008,526 | 7/1935 | Wappler et al. . | |
| 2,022,065 | 11/1935 | Wappler . | |
| 2,047,535 | 7/1936 | Wappler . | |
| 2,118,631 | 5/1938 | Wappler . | |
| 2,710,000 | 6/1955 | Cromer et al. . | |
| 3,230,957 | 1/1966 | Seifert . | |
| 3,339,542 | 9/1967 | Howell . | |
| 3,556,079 | 1/1971 | Omizo et al. | 128/2 |
| 3,595,239 | 7/1971 | Petersen . | |
| 3,598,108 | 8/1971 | Jamshidi . | |
| 3,682,162 | 8/1972 | Colyer . | |
| 3,828,780 | 8/1974 | Morrison, Jr. . | |
| 3,835,842 | 9/1974 | Iglesias . | |
| 3,840,016 | 10/1974 | Lindemann . | |
| 3,850,175 | 11/1974 | Iglesias . | |
| 3,858,577 | 1/1975 | Bass et al. . | |
| 3,884,237 | 5/1975 | O'Malley et al. . | |
| 3,924,628 | 12/1975 | Droegemueller et al. . | |
| 3,939,840 | 2/1976 | Storz . | |
| 3,942,530 | 3/1976 | Northeved . | |
| 3,948,270 | 4/1976 | Hasson . | |
| 3,991,770 | 11/1976 | Leveen . | |
| 4,011,872 | 3/1977 | Komiya . | |
| 4,119,102 | 10/1978 | Leveen . | |
| 4,121,592 | 10/1978 | Whalley . | |
| 4,136,566 | 1/1979 | Christensen . | |
| 4,137,920 | 2/1979 | Bonnet . | |
| 4,154,246 | 5/1979 | Leveen . | |
| 4,204,549 | 5/1980 | Paglione . | |
| 4,224,929 | 9/1980 | Furihata . | |
| 4,228,809 | 10/1980 | Paglione | 128/804 |
| 4,237,898 | 12/1980 | Whalley . | |
| 4,267,828 | 5/1981 | Matsuo . | |
| 4,295,467 | 10/1981 | Mann et al. . | |
| 4,307,720 | 12/1981 | Weber, Jr. . | |
| 4,311,145 | 1/1982 | Esty et al. . | |
| 4,311,154 | 1/1982 | Sterzer et al. . | |
| 4,312,364 | 1/1982 | Convert et al. . | |
| 4,375,220 | 3/1983 | Matvias . | |
| 4,397,314 | 8/1983 | Vaguine . | |
| 4,402,311 | 9/1983 | Hattori . | |
| 4,405,314 | 9/1983 | Cope . | |
| 4,411,266 | 10/1983 | Cosman . | |
| 4,448,198 | 5/1984 | Turner . | |
| 4,452,236 | 6/1984 | Utsugi . | |
| 4,470,407 | 9/1984 | Hussein | 606/2 |
| 4,494,539 | 1/1985 | Zenitani et al. . | |
| 4,552,554 | 11/1985 | Gould et al. . | |
| 4,562,838 | 1/1986 | Walker . | |
| 4,565,200 | 1/1986 | Cosman . | |
| 4,568,329 | 2/1986 | Mahurkar . | |
| 4,580,551 | 4/1986 | Siegmund et al. . | |
| 4,594,074 | 6/1986 | Anderson et al. . | |
| 4,601,296 | 7/1986 | Yerushalmi . | |
| 4,612,940 | 9/1986 | Kasevich et al. . | |
| 4,658,836 | 4/1987 | Turner . | |
| 4,660,560 | 4/1987 | Klein . | |
| 4,669,475 | 6/1987 | Turner . | |
| 4,672,962 | 6/1987 | Hershenson . | |
| 4,676,258 | 6/1987 | Inokuchi et al. . | |
| 4,681,122 | 7/1987 | Winters et al. . | |
| 4,682,596 | 7/1987 | Bales et al. . | |
| 4,697,595 | 10/1987 | Breyer et al. . | |
| 4,700,716 | 10/1987 | Kasevich et al. . | |
| 4,706,681 | 11/1987 | Breyer et al. . | |
| 4,709,698 | 12/1987 | Johnston et al. . | |
| 4,719,914 | 1/1988 | Johnson . | |
| 4,753,223 | 6/1988 | Bremer . | |
| 4,765,331 | 8/1988 | Petruzzi et al. . | |
| 4,769,005 | 9/1988 | Ginsburg et al. . | |
| 4,774,949 | 10/1988 | Fogarty . | |
| 4,776,086 | 10/1988 | Kasevich et al. . | |
| 4,781,186 | 11/1988 | Simpson et al. . | |
| 4,784,638 | 11/1988 | Ghajar et al. . | |
| 4,785,829 | 11/1988 | Convert et al. . | |
| 4,798,215 | 1/1989 | Turner . | |
| 4,800,899 | 1/1989 | Elliott . | |
| 4,805,616 | 2/1989 | Pao . | |
| 4,813,429 | 3/1989 | Eshel et al. . | |
| 4,817,601 | 4/1989 | Roth et al. . | |
| 4,818,954 | 4/1989 | Flachenecker et al. . | |
| 4,822,333 | 4/1989 | Lavarenne . | |
| 4,823,791 | 4/1989 | D'Amelio et al. . | |
| 4,823,812 | 4/1989 | Eshel et al. . | |
| 4,860,744 | 8/1989 | Johnson et al. . | |
| 4,865,047 | 9/1989 | Chou et al. . | |
| 4,872,458 | 10/1989 | Kanehira et al. . | |
| 4,887,615 | 12/1989 | Taylor . | |
| 4,893,623 | 1/1990 | Rosenbluth . | |
| 4,896,671 | 1/1990 | Cunningham et al. . | |
| 4,898,577 | 2/1990 | Badger . | |
| 4,905,667 | 3/1990 | Foerster et al. . | |
| 4,906,230 | 3/1990 | Maloney et al. . | |
| 4,907,589 | 3/1990 | Cosman . | |
| 4,911,148 | 3/1990 | Sosnowski et al. . | |
| 4,911,173 | 3/1990 | Terwilliger . | |
| 4,919,129 | 4/1990 | Weber, Jr. et al. . | |
| 4,920,978 | 5/1990 | Colvin . | |
| 4,932,958 | 6/1990 | Reddy et al. . | |
| 4,936,281 | 6/1990 | Stasz . | |
| 4,940,064 | 7/1990 | Desai . | |
| 4,943,290 | 7/1990 | Rexroth | 606/49 |
| 4,946,449 | 8/1990 | Davis, Jr. . | |
| 4,949,706 | 8/1990 | Thon . | |
| 4,950,267 | 8/1990 | Ishihara et al. | 606/12 |
| 4,955,377 | 9/1990 | Lennox et al. . | |
| 4,961,435 | 10/1990 | Kitagawa et al. . | |
| 4,966,597 | 10/1990 | Cosman . | |
| 4,967,765 | 11/1990 | Turner et al. . | |
| 4,982,724 | 1/1991 | Saito et al. . | |
| 4,998,932 | 3/1991 | Rosen et al. . | |
| 4,998,933 | 3/1991 | Eggers et al. . | |
| 5,002,558 | 3/1991 | Klein et al. . | |
| 5,003,991 | 4/1991 | Takayama et al. . | |
| 5,007,437 | 4/1991 | Sterzer . | |
| 5,007,908 | 4/1991 | Rydell . | |
| 5,010,886 | 4/1991 | Passafaro et al. . | |
| 5,026,959 | 6/1991 | Ito et al. . | |
| 5,029,588 | 7/1991 | Yock et al. . | |
| 5,030,227 | 7/1991 | Rosenbluth et al. . | |
| 5,035,695 | 7/1991 | Weber, Jr. et al. . | |
| 5,035,696 | 7/1991 | Rydell . | |
| 5,045,056 | 9/1991 | Behl . | |
| 5,045,072 | 9/1991 | Castillo . | |
| 5,055,109 | 10/1991 | Gould et al. . | |
| 5,057,105 | 10/1991 | Malone et al. . | |
| 5,057,106 | 10/1991 | Kasevich et al. . | |
| 5,057,107 | 10/1991 | Parins . | |
| 5,059,851 | 10/1991 | Corl et al. . | |
| 5,060,660 | 10/1991 | Gambale et al. . | |
| 5,071,418 | 12/1991 | Rosenbaum | 606/45 |
| 5,080,660 | 1/1992 | Buelna . | |
| 5,083,565 | 1/1992 | Parins . | |
| 5,084,044 | 1/1992 | Quint . | |
| 5,100,423 | 3/1992 | Fearnot . | |
| 5,108,415 | 4/1992 | Pinchuk et al. . | |
| 5,109,859 | 5/1992 | Jenkins . | |
| 5,116,615 | 5/1992 | Gokcen et al. . | |
| 5,120,316 | 6/1992 | Morales et al. . | |
| 5,122,137 | 6/1992 | Lennox | 606/42 |
| 5,135,525 | 8/1992 | Biscoping et al. . | |
| 5,150,717 | 9/1992 | Rosen et al. . | |

| | | |
|---|---|---|
| 5,170,787 | 12/1992 | Lindegren . |
| 5,178,620 | 1/1993 | Eggers et al. . |
| 5,179,962 | 1/1993 | Dutcher et al. . |
| 5,190,539 | 3/1993 | Fletcher et al. . |
| 5,195,965 | 3/1993 | Shantha . |
| 5,195,968 | 3/1993 | Lundquist et al. . |
| 5,197,963 | 3/1993 | Parins ............ 606/41 |
| 5,201,732 | 4/1993 | Parins et al. . |
| 5,207,672 | 5/1993 | Roth . |
| 5,220,927 | 6/1993 | Astrahan et al. . |
| 5,222,953 | 6/1993 | Dowlatshahi . |
| 5,228,441 | 7/1993 | Lundquist . |
| 5,234,004 | 8/1993 | Hascoet et al. ......... 607/102 |
| 5,235,964 | 8/1993 | Abenaim . |
| 5,249,585 | 10/1993 | Turner et al. ............ 607/99 |
| 5,254,088 | 10/1993 | Lundquist et al. . |
| 5,257,451 | 11/1993 | Edwards et al. . |
| 5,273,535 | 12/1993 | Edwards et al. . |
| 5,275,162 | 1/1994 | Edwards et al. . |
| 5,281,213 | 1/1994 | Milder et al. . |
| 5,281,217 | 1/1994 | Edwards et al. . |
| 5,281,218 | 1/1994 | Imran . |
| 5,287,845 | 2/1994 | Faul et al. . |
| 5,290,286 | 3/1994 | Parins . |
| 5,293,868 | 3/1994 | Nardella . |
| 5,293,869 | 3/1994 | Edwards et al. . |
| 5,299,559 | 4/1994 | Bruce et al. . |
| 5,300,068 | 4/1994 | Rosar et al. . |
| 5,300,069 | 4/1994 | Hunsberger et al. . |
| 5,300,070 | 4/1994 | Gentelia et al. . |
| 5,300,099 | 4/1994 | Rudie . |
| 5,301,687 | 4/1994 | Wong et al. . |
| 5,304,134 | 4/1994 | Kraus et al. . |
| 5,304,214 | 4/1994 | Deford . |
| 5,309,910 | 5/1994 | Edwards et al. . |
| 5,313,943 | 5/1994 | Houser et al. . |

FOREIGN PATENT DOCUMENTS

| | | |
|---|---|---|
| 521264A2 | 1/1993 | European Pat. Off. . |
| 2848484 | 5/1979 | Germany . |
| 2941060 | 4/1980 | Germany ............... 606/48 |
| 3218314 | 6/1983 | Germany . |
| 3247793 | 7/1983 | Germany ............... 606/47 |
| 3844131 | 12/1988 | Germany . |
| 3838840 | 5/1990 | Germany . |
| 2121675 | 5/1990 | Japan . |
| 9007303 | 7/1990 | WIPO . |
| WO911213 | 8/1991 | WIPO . |
| 9116859 | 11/1991 | WIPO . |
| 9207622 | 5/1992 | WIPO . |
| WO92/10142 | 6/1992 | WIPO . |
| 9210142 | 6/1992 | WIPO . |
| 9221278 | 12/1992 | WIPO . |
| 9221285 | 12/1992 | WIPO . |
| 9304727 | 4/1993 | WIPO . |
| 9308756 | 5/1993 | WIPO . |
| 9308755 | 5/1993 | WIPO . |
| 9320893 | 10/1993 | WIPO . |
| 9308757 | 10/1993 | WIPO . |
| 9320767 | 10/1993 | WIPO . |
| 9320768 | 10/1993 | WIPO . |
| 9320886 | 10/1993 | WIPO . |
| WO93/25136 | 12/1993 | WIPO . |
| 9403759 | 2/1994 | WIPO . |
| 9404222 | 3/1994 | WIPO . |
| 9405226 | 3/1994 | WIPO . |
| 9406377 | 3/1994 | WIPO . |
| 9407410 | 4/1994 | WIPO . |
| 9407411 | 4/1994 | WIPO . |
| 9407412 | 4/1994 | WIPO . |
| 9407413 | 4/1994 | WIPO . |
| 9407441 | 4/1994 | WIPO . |
| 9407446 | 4/1994 | WIPO . |
| 9407549 | 4/1994 | WIPO . |

OTHER PUBLICATIONS

Perinchery, Narayan, "Neoplasms of the Prostate Gland." pp. 378–409 (Date Unknown).

Urology 5th ed., Storz, Jan. 1992.

Transuretheral μwave Thermotherapy for Prostatism: Early Mayo Foundation Experience: Blute, Mayo Clinic Proceedings: vol. 67 May 1992 pp. 417–421.

New Therapies for Benign Prostatic Hyperplasia, Editorial Bruskewitz, Mayo Clinic Proceedings vol. 67 May 1992 pp. 493–495.

Industry Strategies, Urology: "A Multi Billion Dollar Market . . . " Stephen Scala Nov. 19, 1991, pp. 1–32.

U.I. Dept. of Health and Human Services, MMWR 41: 401–404 vol. 41, No. 23, (Jun. 12, 1992).

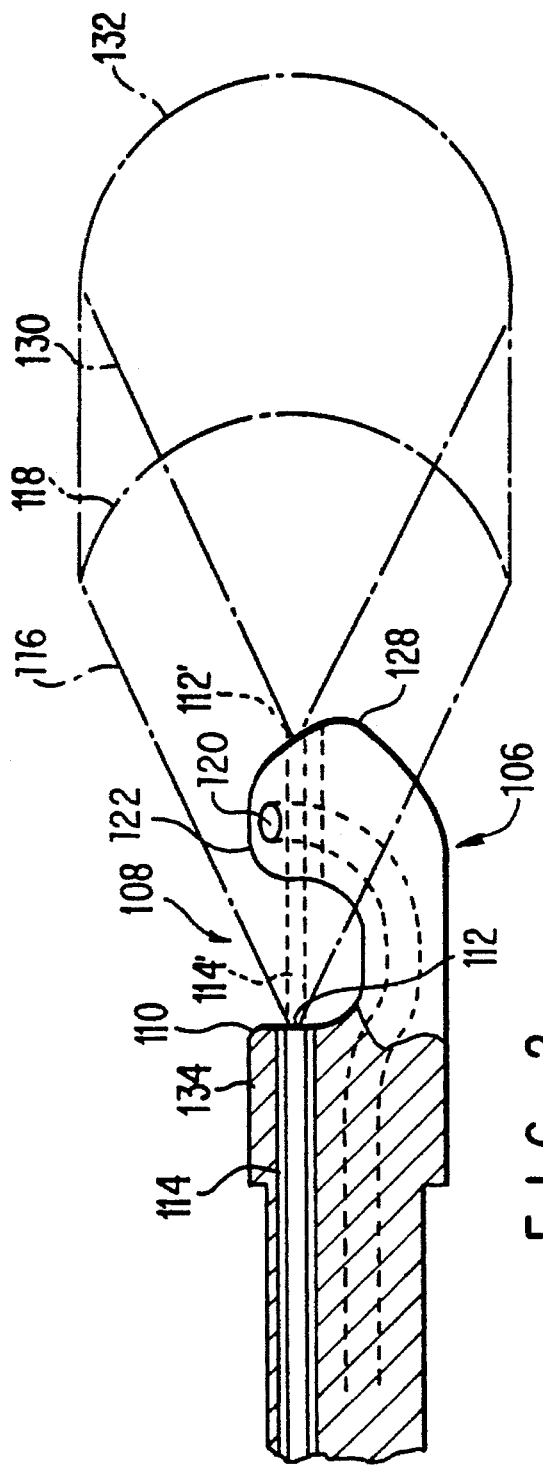
FIG. 2
FIG. 3
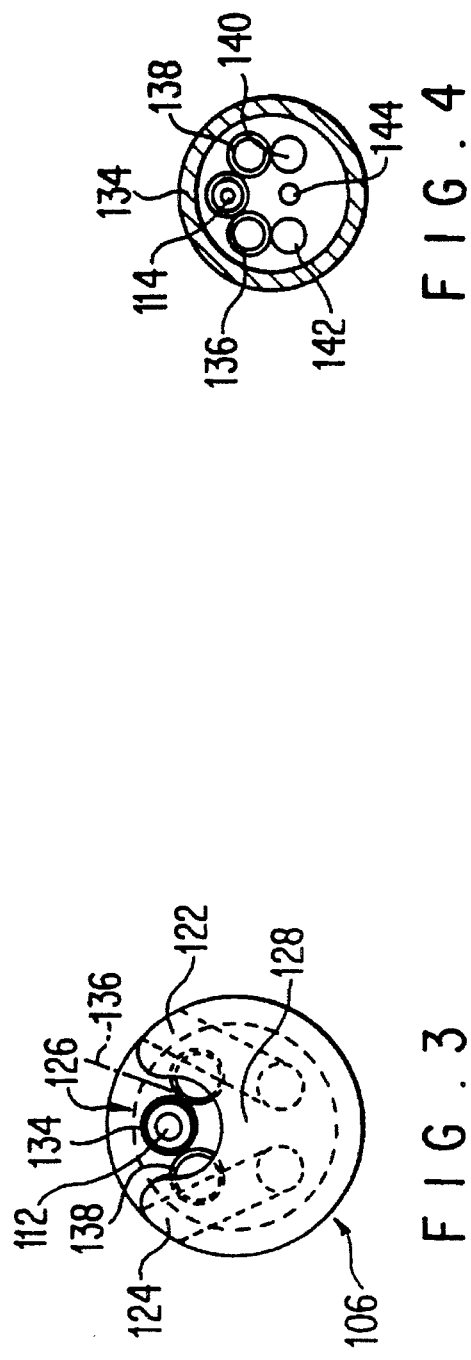
FIG. 4

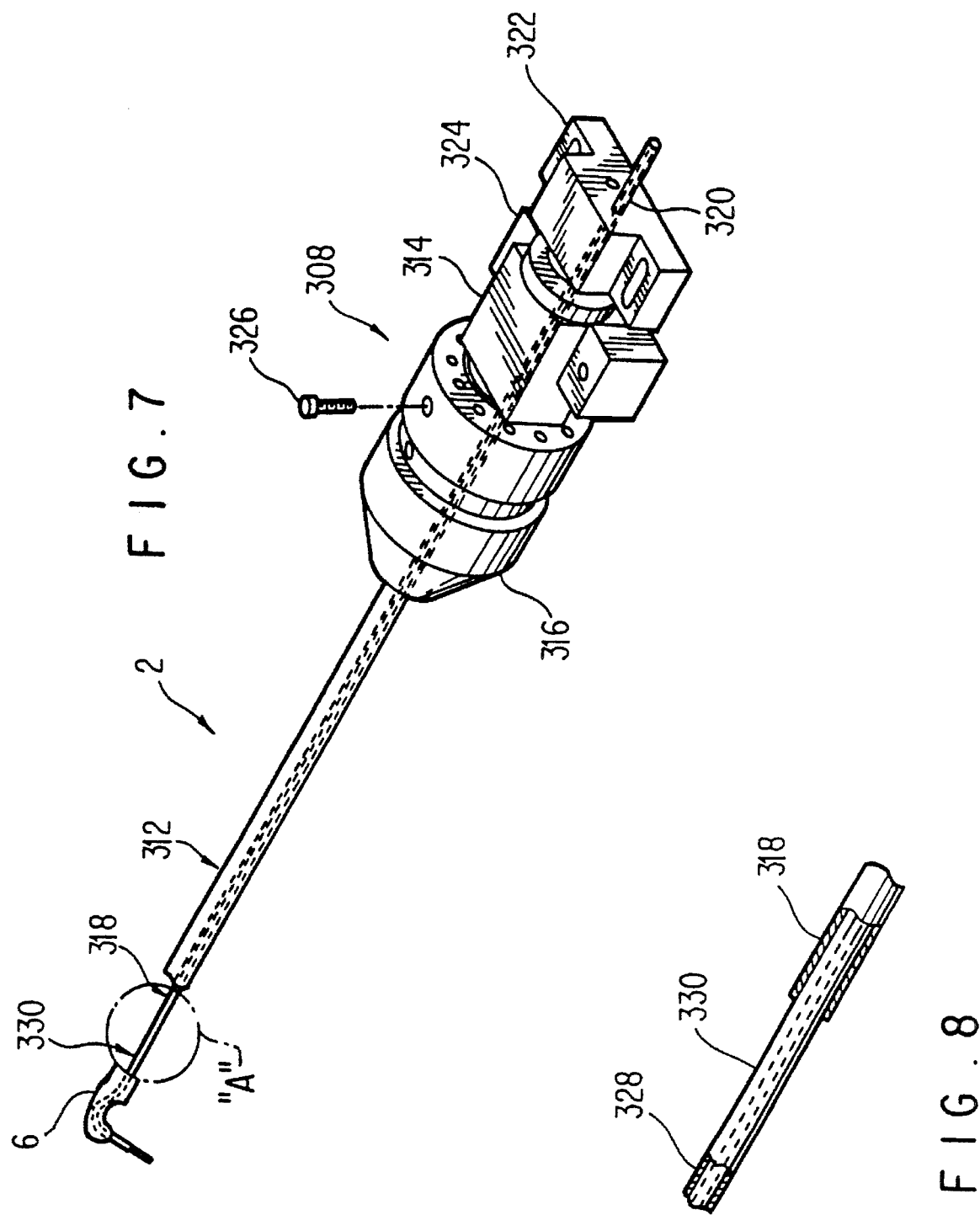

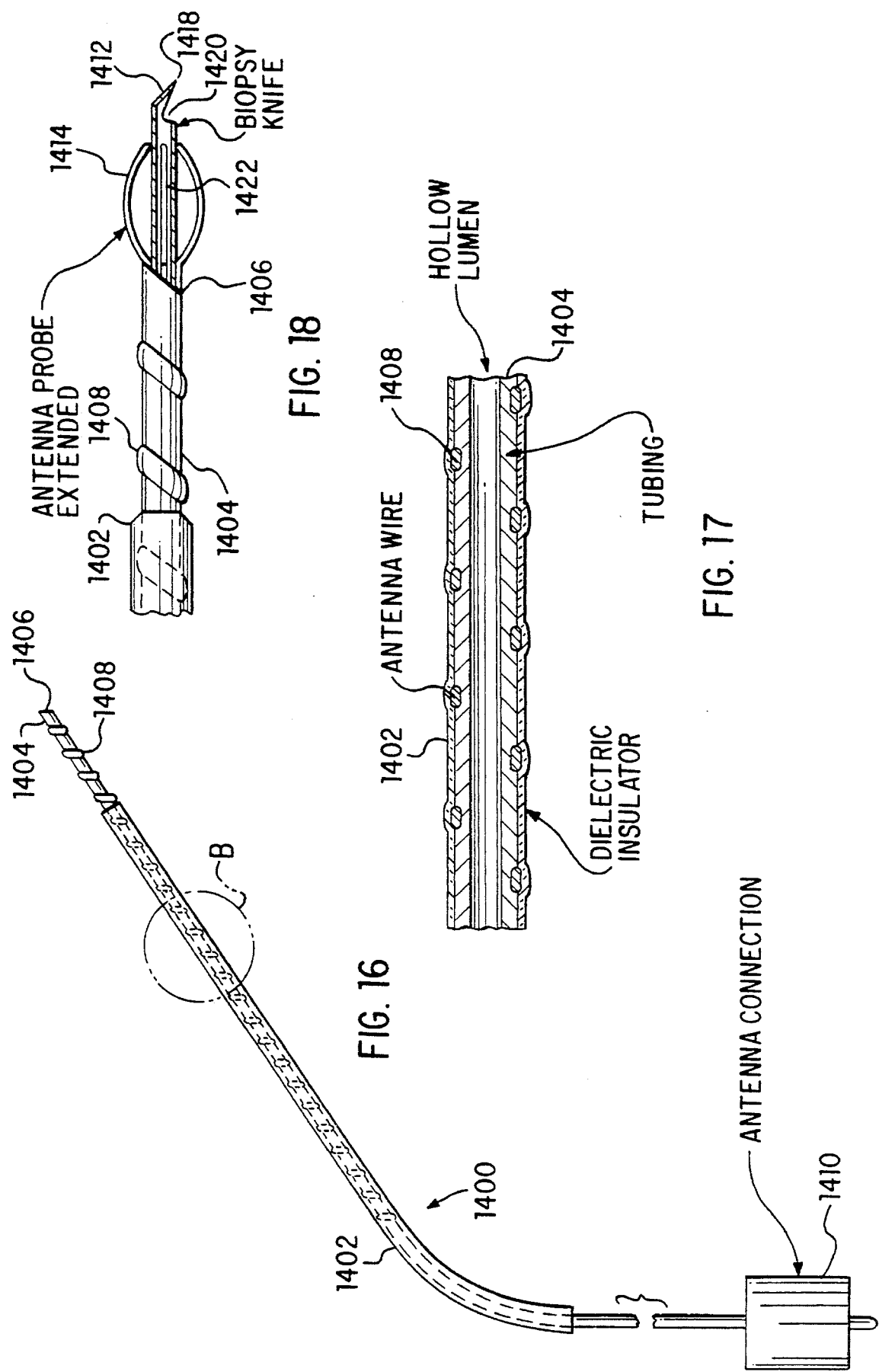

MEDICAL PROBE WITH BIOPSY STYLET

RELATIONSHIP TO COPENDING APPLICATION

This application is a continuation-in-part of applications Ser. No. 07/929,638, filed Aug. 12, 1992, now abandoned; Ser. No. 08/012,370, filed Feb. 2, 1993, now U.S. Pat. No. 5,370,675; and Ser. No. 08/062,364, filed May 13, 1993, now U.S. Pat. No. 5,435,805; the entire contents of which are incorporated herein by reference.

FIELD OF THE INVENTION

This invention is directed to unique methods and apparatus for penetrating body tissues to a target tissue for purposes of obtaining a biopsy tissue sample, and, optionally, for other medical purposes such as tissue destruction and fluid substance delivery, for example. The device penetrates tissue to the precise target selected in order to obtain the sample and optionally to deliver energy to the tissue and/or deliver substances. It limits this activity to the precise preselected site, thereby minimizing trauma to normal surrounding tissue and achieving a greater medical benefit. This apparatus is a catheter-like device for positioning a biopsy and optional treatment assembly in the area or organ selected for examination and medical treatment with one or more stylets in the catheter, mounted for extension from a styler port in the side of the catheter through surrounding tissue to the tissue targeted for medical activity.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of a target tissue in the body, or the proximity of the target tissue to easily damaged, critical body organs, nerves, or other components.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling. The association of BPH with aging has been shown by the incidence of BPH to exceed 50% in men over 50 years of age and increases in incidence to over 75% in men over 80 years of age. Symptoms of urinary obstruction occur most frequently between the ages of 65 and 70 when approximately 65% of men in this age group have prostatic enlargement.

Currently there is no nonsurgical method of treatment of BPH which has proven to be effective. In addition, the surgical procedures available are not totally satisfactory. Currently patients suffering from the obstructive symptoms of this disease are provided with few options: continue to cope with the symptoms (i.e., conservative management), submit to drug therapy at early stages, or submit to surgical intervention. More than 430,000 patients per year in the United States undergo surgery for removal of prostatic tissue. These represent less than five percent of men exhibiting clinical significant symptoms.

Those suffering from BPH are often elderly men, many with additional health problems which increase the risk of surgical procedures. Surgical procedures for the removal of prostatic tissue are associated with a number of hazards including anesthesia associated morbidity, hemorrhage, coagulopathies, pulmonary emboli and electrolyte imbalances. These procedures performed currently can also lead to cardiac complications, bladder perforation, incontinence, infection, urethral or bladder neck stricture, retention of prostatic chips, retrograde ejaculation, and infertility. Due, to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, dilation of the kidney pelves, chronic infection, dilation of ureters, etc.) which is not without significant consequences. In addition, a significant number of patients with symptoms sufficiently severe to warrant surgical intervention are poor operative risks and are poor candidates for prostatectomy. In addition, younger men suffering from BPH who do not desire to risk complications such as infertility are often forced to avoid surgical intervention. Thus the need, importance and value of improved surgical and non-surgical methods for treating BPH is unquestionable.

High-frequency currents are used in electrocautery procedures for cutting human tissue, especially when a bloodless incision is desired or when the operating site is not accessible with a normal scalpel but presents an access for a thin instrument through natural body openings such as the esophagus, intestines, or urethra. Examples include the removal of prostatic adenomas, bladder tumors, or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using an electromagnetic energy which is rapidly dissipated and reduced to a non-destructive level by conduction and convection forces of circulating fluids and other natural body processes.

Microwave, radiofrequency, acoustical (ultrasound) and light energy (laser) devices, and tissue destructive substances have been used to destroy malignant, benign and other types of cells and tissues from a wide variety of anatomic sites ,and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to kill the tissue constricting the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Application of liquids to specific tissues for medical purposes is limited by the ability to obtain delivery without traumatizing intervening tissue and to effect a delivery limited to the specific target tissue. Localized chemotherapy, drug infusions, collagen injections, or injections of agents which are then activated by light, heat or chemicals would be greatly facilitated by a device which could conveniently and precisely place a fluid supply catheter opening at the specific target tissue.

If the operating surgeon desires to take a sample of selected tissue, a biopsy device is utilized. Biopsy devices are well known. U.S. Pat. No. 3,595,217 to Rheinfrank, issued Jul. 27, 1971, describes a prostate biopsy method wherein the physician's finger is guided into the rectum whereupon a biopsy needle is then inserted through the guide and transrectally into the prostate gland. U.S. Pat. No. 3,598,108 to Jamishidi, issued Aug. 10, 1971, describes a biopsy needle with an internal removable sleeve member and stylet. U.S. Pat. No. 4,396,021 to Baumgartner, issued Aug. 2, 1983, describes a prostate biopsy device using a sheath whereupon a harpoon tipped sampling unit is utilized. U.S. Pat. No. 4,600,014 to Beraha, issued Jul. 15, 1986, discloses a core sample biopsy needle arrangement that includes a handle and a guide tube. U.S. Pat. No. 4,989,614 to Dejter, issued Feb. 9, 1991, discloses a fine-needle aspiration biopsy device. U.S. Pat. No. 5,014,717 to Lohrmann, issued May 14, 1991, describes a punch biopsy technique comprising a sleeve-shaped knife and a stylet which slides within the knife. All of these patents, incorporated herein by reference, and others, disclose typical prior art techniques and apparatus for gathering and removing a biopsy sample of tissue for further examination and review by a trained professional.

OBJECTS AND SUMMARY OF THE INVENTION

It is one object of this invention to provide a device for penetrating tissue, through intervening tissues to the precise target tissue selected for a medical action such as tissue ablation and optional substance delivery, limiting this activity to the precise preselected site, thereby minimizing the trauma and achieving a greater medical benefit.

It is another object of this invention to provide medical probe devices with surgical biopsy device directly at the distal end thereof for selective tissue sampling from target tissues.

It is still another object of this invention to provide medical probe devices with a surgical biopsy device capable of obtaining a tissue sample from target tissue.

It is still another object of this invention to provide medical probe devices with a surgical biopsy device capable of obtaining a tissue sample from target tissue in conjunction with an integrated circuit or semiconductor device capable of delivering direct microwave energy for selective ablation applications.

In summary, the device of this invention is a medical probe apparatus comprising a catheter having a stylet guide housing with at least one stylet port in a side thereof and stylet guide means for directing a flexible stylet outward through at least one stylet port and through intervening tissue to targeted tissues. The stylet guide has a biopsy sample device or other tissue manifesting device at the distal end thereof to gather tissue or perform another operation at the point of the desired tissue such as emitting electromagnetic energy as ablative power to target tissues. The stylets comprise thin elongated support means, each support means being enclosed within a non-conductive sleeve, including means at the distal ends of said stylets for selectively emitting electromagnetic energy or for gathering a sample of said target tissue, or both, said electromagnetic energy being delivered as ablative power to said target tissues, with the electromagnetic energy being microwave energy. The non-conductive sleeves are mounted for longitudinal movement on the respective support means to expose a selected portion of the stylet surface in the target tissue.

In another embodiment, a medical probe apparatus is disclosed comprising a catheter having a stylet guide housing with at least one stylet port adjacent the distal end thereof, including stylet guide means for directing a flexible stylet outward through at least one stylet port and through intervening tissue to target tissues, with a stylet positioned in at least one of said stylet guide means, said stylet comprising a thin elongated support means, and means at the distal end of said stylet for gathering a sample of said target tissue. The gathering means comprises a biopsy tissue sampler, said biopsy tissue sampler comprising a biopsy needle means for gathering sample tissue cells, or a sharpened barbed tipped stylet for cutting and gathering said tissue sample, or a clam shell or jaw stylet for gathering said tissue sample. When the biopsy tissue sampler comprises a clam shell or alligator tooth biopsy device for gathering said tissue sample, said biopsy device is opened when deployed by the longitudinal movement of the support means, and being closed on said target tissue to thereby define said tissue sample when said biopsy device is withdrawn into said insulating sleeve.

Also the biopsy tissue sampler may comprise a harpoon tipped apparatus for gathering said tissue sample. The biopsy tissue sampler would comprise a core sampling apparatus for gathering said tissue sample, wherein said core sampling apparatus comprises a hollow tube having a sharpened end for facilitating the penetration into and gathering of said sample tissue. In addition, if said biopsy tissue sampler comprises a hollow tube, having an aperture along the lateral side thereof adjacent the distal end of said tube, the tissue sample being drawn into said hollow tube by a negative pressure applied to said hollow tube, said tissue sample being excised from said target tissue when said hollow tube is withdrawn into said insulating sleeve. The hollow tube may be harpoon shaped, having an aperture therein and a sharpened tip to facilitate the penetration into said target tissue.

Further the biopsy tissue; sampler comprises a clam shell or alligator tooth apparatus for gathering said tissue sample, with said biopsy device being opened when deployed by the longitudinal movement of said support means, and being closed on said target tissue to thereby define said tissue sample when said biopsy device is withdrawn into said insulating sleeve.

Another embodiment also includes means at the distal end of said stylet for emitting electromagnetic energy, said emitting means being energized selectively with said gathering means or independently therefrom. Here said means for emitting electromagnetic energy comprises a microwave antenna and said gathering means comprises a biopsy tissue sampler, said stylet emitting electromagnetic energy selectively with said biopsy tissue sampler or independently therefrom. The antenna wire is curled around said insulating sleeve from the proximal end to the distal end of said insulating sleeve.

BRIEF DESCRIPTION OF THE DRAWINGS

For a more complete understanding of the invention, reference may be had to the following detailed description of the invention in conjunction with the drawings wherein:

FIG. 2 is a fragmented cross-sectional view of a preferred catheter tip and styler guide housing of this invention;

FIG. 3 is distal end view of the catheter tip and style guide housing shown in FIG. 2;

FIG. 4 is a proximal end view of the unassembled catheter tip and stylet guide housing shown in FIG. 2, showing the lumina for the components thereof;

FIG. 7 is an isometric view of the adjuster block and tension tube assembly of the RF ablation catheter shown in FIG. 6;

FIG. 8 is a detailed view "A" of the tension tube connections shown in FIG. 7;

FIG. 16 is a side view of another embodiment of a biopsy sampling stylet combining a biopsy knife and an RF antenna;

FIG. 17 is a cross-sectional view of one section of the stylet shown in FIG. 16; and FIG. 18 is a cross-sectional view of the distal end of the stylet shown in FIG. 16 combining the antenna probe and biopsy knife.

DETAILED DESCRIPTION OF THE INVENTION

Figure 1:
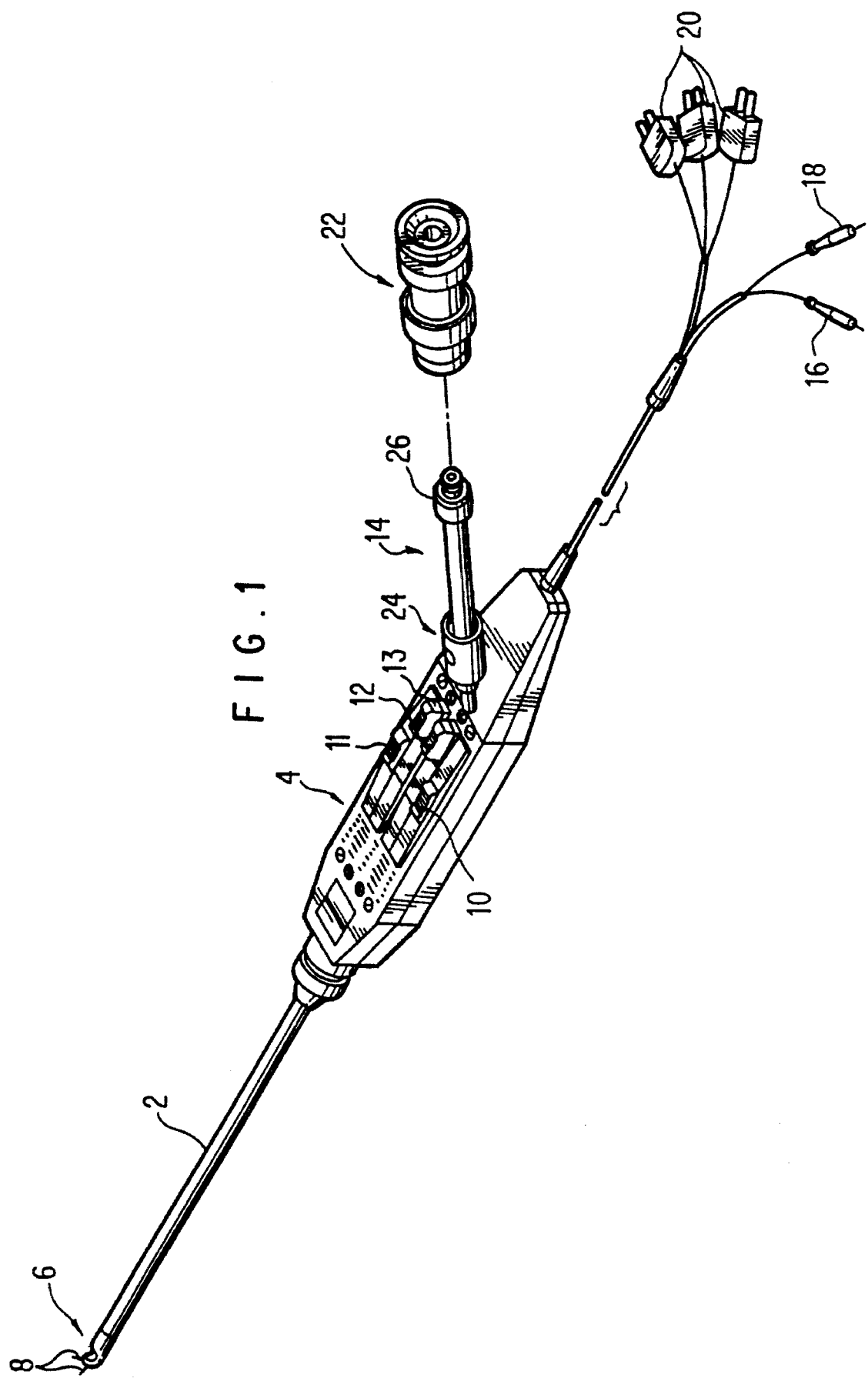
FIG. 1 is an isometric view of an RF ablation catheter embodiment with a fiber optic viewing accessory.

The device of this invention provides a precise controlled positioning of a treatment stylet in a tissue targeted for treatment, ablation, or sampling from a catheter positioned in the vicinity of targeted tissues.

The term "stylet" as used hereinafter is defined to include both solid and hollow probes which are adapted to be passed from a catheter port through normal tissue to targeted tissues. The styler is shaped to facilitate easy passage through tissue. It can be a solid wire, thin rod, or other solid shape or it can be a thin hollow tube or other shape having a longitudinal lumen for introducing fluids to or removing materials from a site. The stylet can also be a thin hollow tube or other hollow shape, the hollow lumen thereof containing a reinforcing or functional rod or tube such as a laser fiber optic. The stylet preferably has a sharpened end to reduce resistance and trauma when it is pushed through tissue to a target site. As will be hereafter described, the stylet can also include biopsy sample gathering, laser light emitting, and microwave apparatus, as well.

The stylet can be designed to provide a variety of medically desired treatments of a selected tissue. As a resistance heater, radiofrequency electrode, laser light emitter, or microwave antenna, it can be used to ablate or destroy targeted tissues. As a hollow tube, it can be used to deliver a treatment fluid such as a liquid to targeted tissues. The liquid can be a simple solution or a suspension of solids, for example, colloidal particles, in a liquid. Since the stylet is very thin, it can be directed from the catheter through intervening normal tissue with a minimum of trauma to the normal tissue. As a biopsy sample gatherer, a sample specimen of target tissue may be taken and removed for further external histological analysis and examination.

The device and method of this invention provide a more precise, controlled medical treatment which is suitable for gathering or destroying cells of medically targeted tissues throughout the body, both within and external to body organs. The device and method are particularly useful for treating benign prostate hyperplasia (BPH), and the device and its use are hereinafter described with respect to BPH, for purposes of simplifying the description thereof. It will be readily apparent to a person skilled in the art that the apparatus and method can be used to gather or destroy body tissues in any body cavities or tissue locations that are accessible by percutaneous or endoscopic catheters, and is not limited to the prostate. Application of the device and method in all of these organs and tissues are intended to be included within the scope of this invention.

BPH is a condition which arises from the benign replication and growth of cells in the prostate, forming glandular and stromal nodules which expand the prostate and constrict the opening of the prostatic urethra. Glandular nodules arc primarily concentrated within the transition zone, and stromal nodules within the periurethral region. Traditional treatments of this condition have included surgical removal of the entire prostate gland, digital removal of the adenoma, as well as transurethral resection of the urethral canal and prostate to remove tissue and widen the passageway. One significant and serious complication associated with these procedures is iatrogenic sterility. More recently, laser treatment has been employed to remove tissue, limiting bleeding and loss of body fluids. Balloons have also been expanded within the urethra to enlarge its diameter, with and without heat, but have been found to have significant limitations.

Microwave therapy has been utilized with some success by positioning a microwave antenna within the prostatic urethra and generating heat in the tissue surrounding the urethra with a microwave field. Coolants are sometimes applied within the catheter shaft to reduce the temperature of the urethral wall. This necessitates complicated mechanisms to provide both cooling of the immediately adjacent tissues while generating heat in the more distant prostatic tissue. This technique is similar to microwave hyperthermia. Similarly, radiofrequency tissue ablation with electrodes positioned within the urethra exposes the urethral wall to destructive temperatures. To avoid this, temperature settings required to protect the urethra must be so low that the treatment time required to produce any useful effect is unduly extended, e.g. up to three hours of energy application.

One embodiment of the device of this invention previously disclosed in a parent application uses the urethra to access the prostate and positions RF electrode stylets directly into the tissues or nodules to be destroyed. The portion of the stylet conductor extending from the urethra to targeted tissues is enclosed within a longitudinally adjustable sleeve shield which prevents exposure of the tissue adjacent to the sleeve to the RF current. The sleeve movement is also used to control the amount of energy per unit surface area which is delivered by controlling the amount of electrode exposed. Thus the ablation is confined to the tissues targeted for ablation, namely those causing the mechanical constriction. Other aspects of the invention will become apparent from the drawings and accompanying descriptions of the device and method of this invention. It will be readily apparent to a person skilled in the art that this procedure can be used in many areas of the body for percutaneous approaches and approaches through body orifices.

FIG. 1 is an isometric view of an ablation catheter embodiment of this invention with a fiber optic viewing accessory. The flexible catheter 2, attached to handle 4, has a terminal stylet guide 6 with two stylets 8. The handle has stylet sleeve tabs 10 and 11 and electrode tabs 12 and 13 as will be described in greater detail hereinafter. The handle 4 is also connected to a optical viewing assembly 14 and RF power connector 16, transponder connector 18 and thermocouple connectors 20. The portions of the catheter 2 leading from the handle 4 to the stylet guide tip 6 can optionally have a graduated stiffness. For example, the catheter can be designed to be more stiff near the handle and more flexible near the tip, or any other stiffness profiles. The catheter can be constructed of an inner slotted stainless steel tube with outer flexible sleeve such as is described in copending application Ser. No. 790,648 filed Aug. 11, 1991 (corresponding to published Australian patent application Ser. No. 9210858), the entire contents of which are incorporated herein by reference. It can also be made of coiled or braided wire to which an outer sleeve is bonded.

The fiber optic viewing assembly in this embodiment includes a lens focusing assembly 22, a lens viewing assembly support connector 24 assembly attached to a male quick disconnect connector 26 by flexible tubing 28.

FIG. 2 is a fragmented cross-sectional view of a preferred catheter tip and stylet guide housing of this invention. The solid catheter tip 106 has a lateral depression or saddle 108 therein having a central axis approximately perpendicular to a plane through the central axis of the tip. The depression 108 has a proximal wall 110. The depression 108 can extend up to approximately half of the thickness of the housing, but at least sufficiently to unblock the viewing surface of the viewing tip 112 of the fiber optic 114. The fiber optic viewing tip 112, when positioned at the opening in wall 110, provides a field of view with lateral margins 116 and a terminal margin 118. This includes the path of stylets extended outward through ports 120.

FIG. 3 a distal end view of the catheter tip and style guide housing shown in FIG. 2. The proximal end of depression 108 is split to form two projections or ears 122 and 124 which define a longitudinal or axial or longitudinal groove or saddle 126 extending from the depression 108 to the terminal tip 128 of the ,catheter 106. Groove 126 opens the field of view for the viewing tip 112 when in the solid line position shown in FIG. 2 and permits extension of the fiber optic and its tip through the longitudinal groove to the dotted line positions 114' and 112'. In the latter position, the field of vision has side margins 130 and a terminal margin 132. This permits the operator to examine the inner duct surfaces ahead of the catheter tip. In an alternative embodiment, the groove 126 can be replaced with a hole in the end of the tip having a size and position to permit extension of the fiber optic 114 therethrough.

The fiber optic 114 is positioned in a passageway 134 which is sufficiently larger than the fiber optic to permit flow of flushing liquid around the fiber optic to the exit in wall 11D. The flushing liquid flow clears debris from the viewing tip. The inner walls of the duct (not shown) surrounding the catheter tip 106 during use confine the liquid flow, so the liquid continues to pass over the fiber optic tip even when it has been advanced to the dotted line position. Return flushing liquid lumina 136 and 138 extend through wall 110 for constant removal of contaminated flushing liquid.

FIG. 4 is a proximal end view of the unassembled catheter tip and stylet guide housing shown in FIG. 2, showing the lumina for the components thereof. The stylets are advanced and retracted through stylet lumina 140 and 142 to the stylet ports 120. The fiber optic is advanced and retracted through fiber optic lumen 134. The contaminated flushing fluid is removed through flushing fluid return lumina 136 and 138. Temperature sensor lumen 144 is used to house leads of a temperature sensor (not shown).

Figure 5:
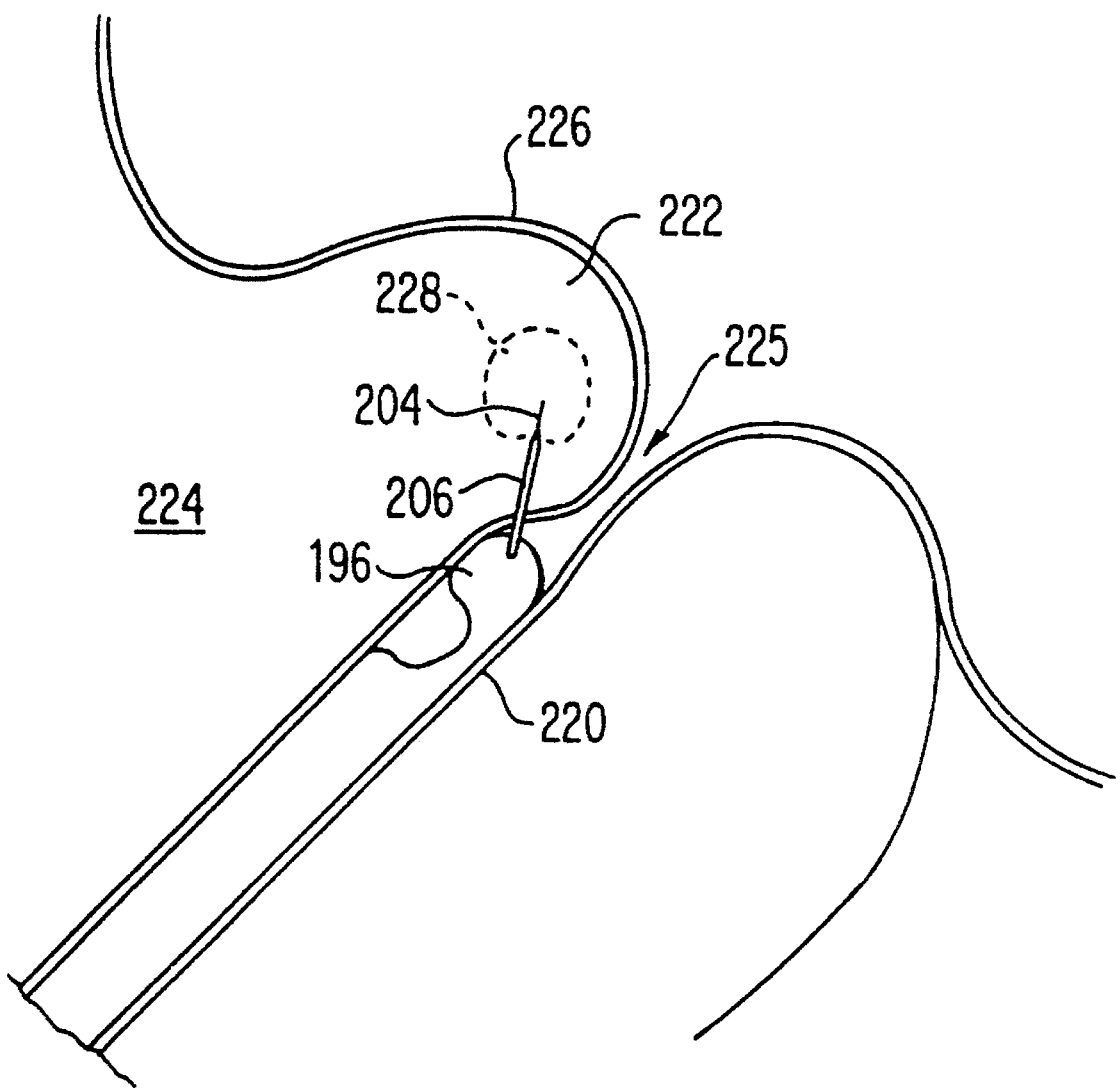
FIG. 5 is a schematic view of one manner of styler deployment into a portion of a prostate protruding into the urinary bladder.

FIG. 5 is a schematic view of a single stylet of FIG. 1 or 2 shown deployed to treat a portion of a prostate protruding into the urinary bladder. The solid catheter tip 196 is positioned at the end of the urethra 220. Cell proliferation in the upper end 222 of the prostate 224 has caused it to protrude into space normally occupied by the urinary bladder, pushing a portion of the bladder wall 226 into the cavity and forming a restriction 225 beyond the end of the urethra. The stylet sleeve 206 and electrode 204 are extended at an angle of about 30° through the urethral wall into a portion of the protruded prostate, and RF current is applied to form the lesion 228. This will reduce the protruded prostate, promoting its retraction from the urethral wall and opening the restriction of the outlet end of the urethra. The catheter having a desired angle can be selected from those having predetermined angles to precisely orient the stylet and effect precise penetration of prostate tissue which extends beyond the end of the urethra, for example.

Figure 6:
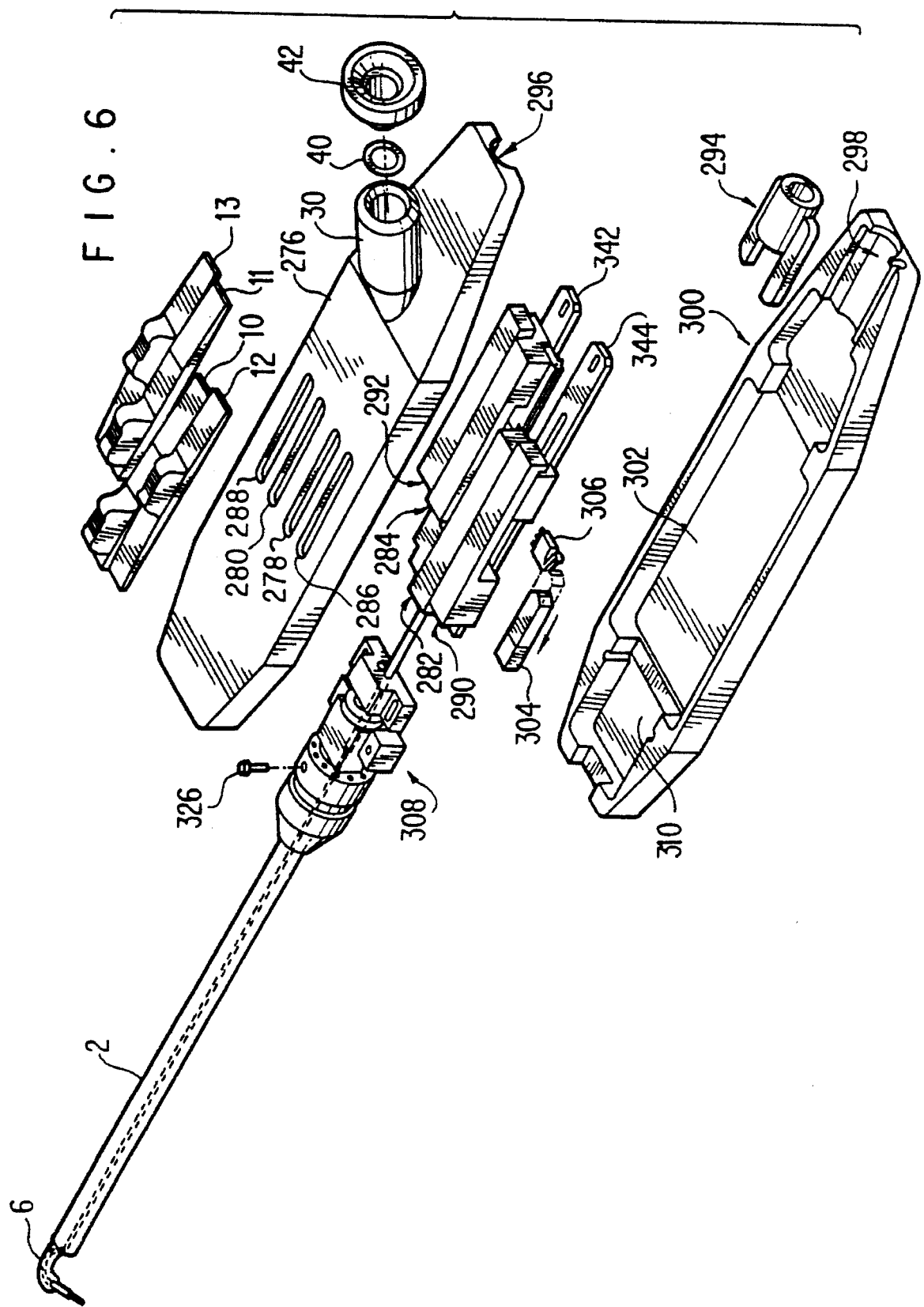
FIG. 6 is an exploded view of the RF ablation catheter shown in FIG. 1.

FIG. 6 is an exploded view of the ablation catheter assembly shown in FIG. 1. The upper handle plate 276 has two central slots 278 and 280 through which the electrode control slides 10 are attached to respective left electrode slide block 282 and right electrode slide block 284. Sleeve control slides 12 and 13 are attached through outer slots 286 and 288 to respective left sleeve slide block 290 and right sleeve slide block 292. Fiber optic receptor housing 30 is mounted on the proximal surface of the upper handle plate 276. The electrical receptor 294 is received in respective cavities 296 and 298 in the respective upper handle plate 276 and lower handle plate 300 attached thereto. The lower handle plate 300 has a central cavity 302 which accommodates the electrode and sleeve slide blocks and associated elements.

Microswitch activator blocks 304 (only left sleeve block shown) are connected to the sleeve slide blocks 290 and 292. They are positioned to actuate the microswitches 306 when the respective sleeve block (and sleeve attached thereto) have been advanced. The microswitches 306 hold the electromagnetic power circuits open until the respective sleeves are advanced to a position beyond the urethra wall and into the prostate to prevent direct exposure of the urethra to the energized electrodes. Extension of the sleeve 5 mm beyond the guide is usually sufficient to protect the urethra.

The tension-torque tube assembly 308 is mounted in the distal end of the housing in the receptor 310.

FIG. 7 is an isometric view of the adjuster block and tension tube assembly 308 of the ablation catheter shown in FIG. 6. The torque tube 312 extends from the torque coupler 314 through the twist control knob 316 to the stylet guide 6. Bending flexure of the torque tube 312 during use lengthens the path from the handle to the guide tip 6. To prevent a resulting retraction of the style, t sleeve and electrode components when the torque tube 312 is flexed, a tension tube 318 having a fixed length and diameter smaller than the inner diameter of the torque tube 312 is provided. The distal end of the tension tube 318 is securely attached to the stylet guide 6, and the proximal end 320 is secured to the adjuster block 322, for example by an adhesive. The axial or longitudinal position of the adjuster block 322 can be adjusted to insure the stylets are initially positioned just inside the outlet ports in the stylet guide 6. Torque coupler 314 is mounted on the coupler block 324. Twist control knob stop pin 326 extends into a groove (not shown) and limits rotation of the control knob 316.

FIG. 8 is a detailed view "A" of the distal end tension tube connections of the tension tube shown in FIG. 7. The tension tube 318 is securely connected to the proximal end 328 of the stylet guide 6, for example by a length of shrink tubing 330.

Figure 9:
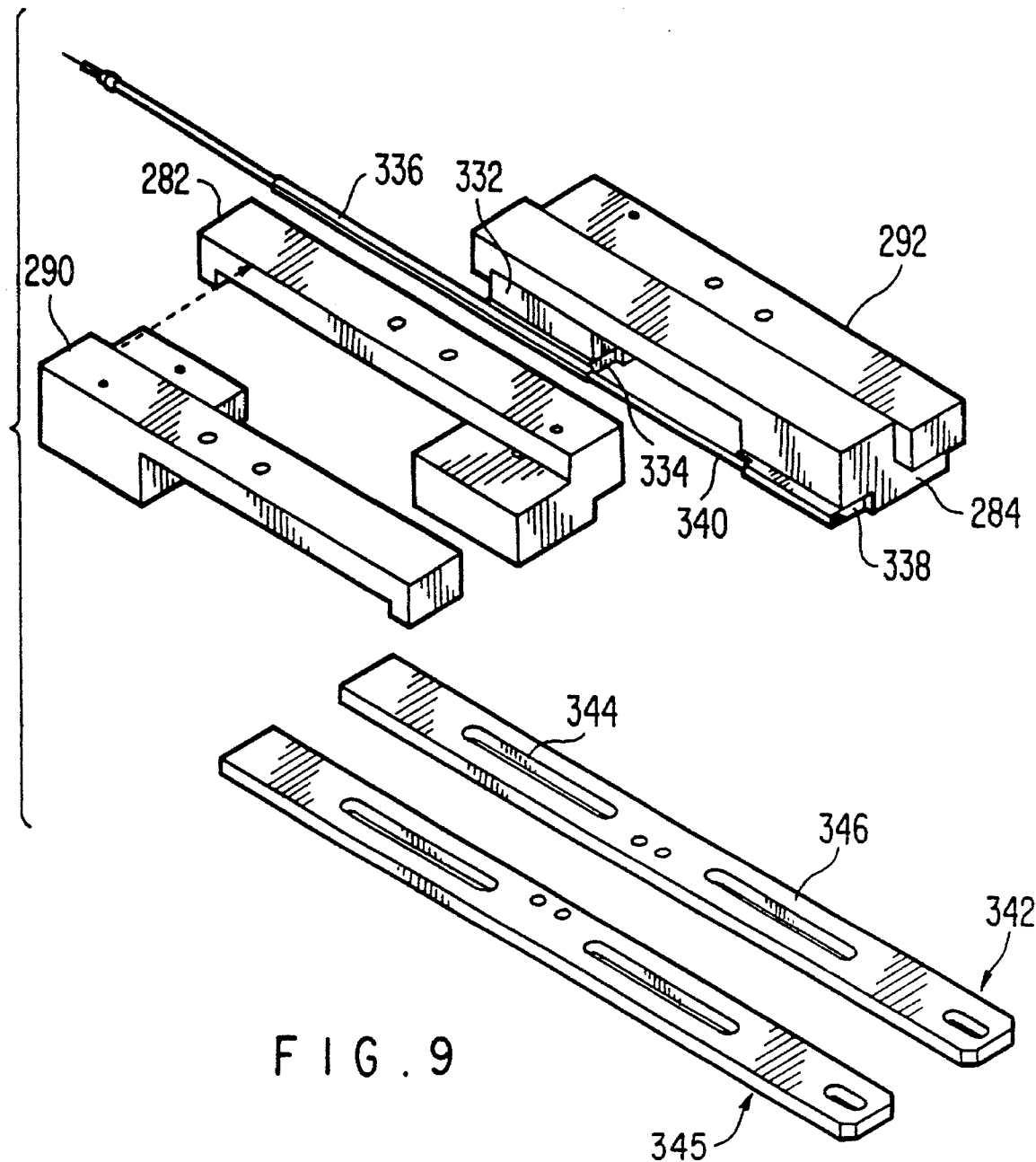
FIG. 9 is an exploded view of the sleeve and electrode slide block assembly of the embodiment shown in FIG. 6.

FIG. 9 is an exploded view of the sleeve and electrode slide block assembly of the embodiment shown in FIG. 6. The right sleeve slide block 292 has a projection 332 which extends inward under the right electrode slide block 284. Right sleeve connector 334 is mounted to the inner end of the projection 332, secured to the end of the proximal end of the sleeve 336. Right electrode connector 338 is attached to an inner surface of the electrode slide block 284 and is secured to the proximal end of electrode 340. The right sleeve and electrode slide blocks 292 and 284 are slidingly attached to the right friction adjustment rail 342 by screws (not shown) through slots 344 and 346, the screws being adjustable to provide sufficient friction between the blocks and the rail 342 to provide secure control over the stylet movement. The left sleeve slide block 290 and left electrode slide block 282 are mirror replicas of the right blocks and are similarly mounted on the left friction rail 345. The left sleeve and electrodes are not shown.

Figure 10:
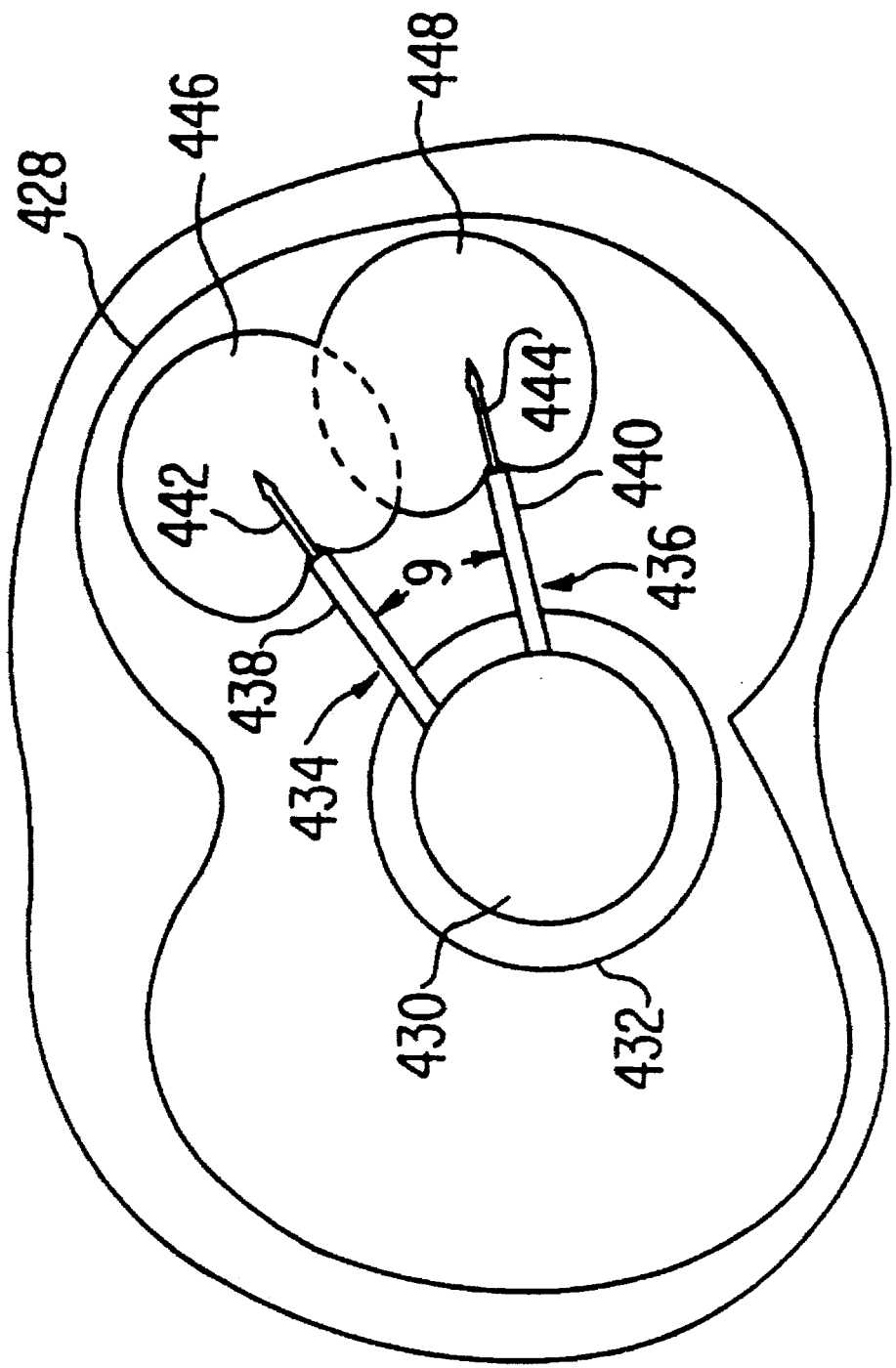
FIG. 10 is a schematic view of a deployment of two stylets in a prostate showing a stylet orientation for overlapping ablation zone method.

FIG. 10 is a schematic view of a deployment of two stylets in a prostate showing stylet orientation for overlapping ablation zone method of this invention as provided, for example, by RF current, or a microwave field. For purposes of illustration, but not by way of limitation, the prostate has been selected for this explanation, and application of this method and assembly to other areas of the body are intended to be included.

The tissues to be treated for the treatment of BPH are located in the transition zone 428 of the prostate. A catheter of this invention 430 has been inserted up the urethra 432 to a position adjacent the prostate. Two stylets 434 and 436 have been passed through the urethra wall 432 through forward movement of tabs 10 and 12 (FIG. 1) and through surrounding tissue into targeted tissues. The non-conducting sleeves 438 and 440 have been retracted by rearward movement of sleeve tabs 10 to expose a portion of the respective electrical conductors 442 and 444 at the end of each stylet. The angle between the axes of the stylets in this embodiment is less than 180°, preferably less than 110°. For most overlapping ablations, angles of 15° to 90°, and more usually from 20° to 70° are most practical. A grounding plate (not shown) is placed on the body exterior.

When electrodes 442 and 444 are supplied with RF current, the circuit from the electrodes to a grounding plate is closed. The current density flowing through the tissue passes through targeted tissues to be treated, creating lesions having the approximate cross-sectional shape of overlapping zones 446 and 448. The current density rapidly decreases as a function of distance, limiting the size of the lesions. In this manner, lesions can be caused to overlap to form a larger lesion, increasing the efficiency of the treatment. It will be readily apparent that these processes can be carried out concurrently, as described, or sequentially, and these variations are intended to be included in this invention.

While the invention described above has utility in the treatment of benign prostate hyperplasia, in some instances a physician may desire to proceed further and actually determine if the prostate contains any cancerous tissue. While the ablation technique described above is effective against BPH, other, and possibly more drastic, procedures may be necessary in the happenstance that the prostate is cancerous. In the possibility that the physician believes that the prostate is cancerous, or contains cancerous tissue or nodules, he or she may desire to examine the suspected tissue by taking a sample of the tissue for histological examination.

The disclosure herein regarding biopsy and tissue gathering of the prostate is not intended to limit the scope of the invention. The principles of the disclosed invention also have utility and applicability to other body tissues.

Figure 11:
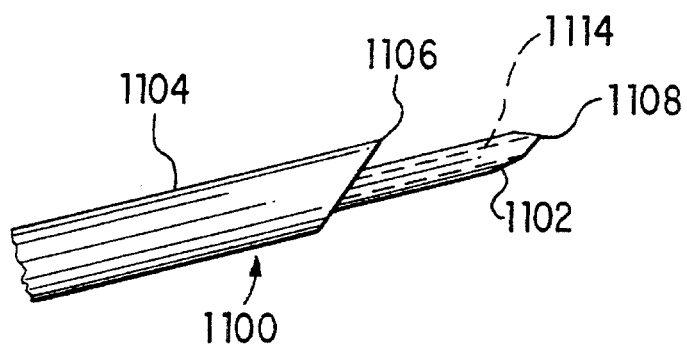
FIG. 11 is a side view of a stylet with a hollow core biopsy sampling apparatus.

FIG. 11 is a side view of a core sampling biopsy stylet 1100. As seen in FIGS. 5, 6, and 7, the stylet comprises a sleeve and an operating electrode. In this embodiment, the electrode has been substituted by the core sampling hollow tube 1102 which is enclosed in sleeve 1104. Sharpened tip 1106 of sleeve 1104 matches the shape of tip 1108 the core sampler stylet 1102. This sharpened edge allows for easier penetration of the tissue leading up to and including the target tissue. After the catheter shown in the previous figures is inserted into the urethra, or other body opening, the sleeve 1104 is extended from the catheter into the urethra wall and into the prostate gland by use of the appropriate stylet sleeve tab 10 or 11 as seen in FIG. 1. At the proper time, the stylet 1102 is extended out of the sleeve 1104 by action of either electrode tabs 12, 13 in FIG. 1. Upon deployment of stylet 1102, a tissue specimen will be cut by the sharp tip 1108 and will be collected in the hollow distal end portion 1114. If desired, the stylet 1102 could be revolved or oscillated around its longitudinal axis to facilitate the cutting action thereof. The core sample stylet 1102 can then be withdrawn into the sleeve 1104, the sleeve 1104 withdrawn into the catheter, and then the catheter completely withdrawn from the body. The biopsied tissue can be withdrawn from the core 1114 of tube 1102 and examined by a medical professional for signs of BPH or cancer.

Figure 12:
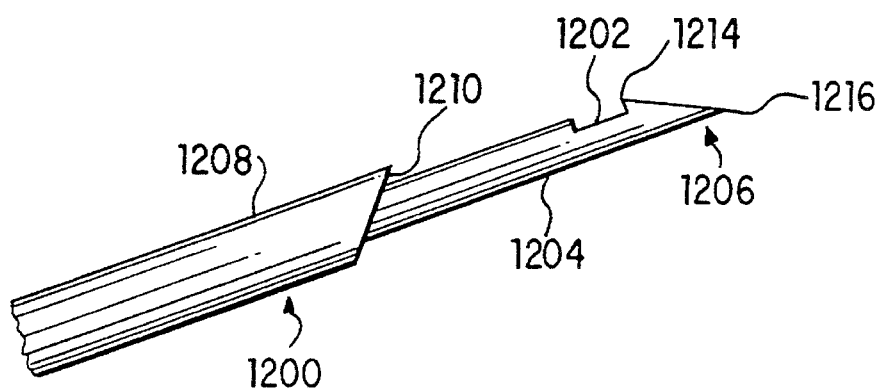
FIG. 12 is a side view of a stylet with a harpoon-shaped biopsy sampling apparatus.

FIG. 12 is a side view of a biopsy sampler stylet assembly 1200 with a harpoon-blade stylet structure 1204. Sleeve 1208 terminates in a forward end 1210 which is tapered to form a blade type surface. Styler shaft 1204 extends through the sleeve 1208 and terminates in the harpoon-shaped structure generally shown at 1206. A harpoon is a barbed, spear-like device which is difficult to remove from a target animal or tissue due to the barbed tip. In this instance, the harpoon-blade structure 1206 is a cylindrical tube 1204 with side port or pocket 1202 as a receptor for gathered tissue. The back of the harpoon 1206 would have sharp, cutting edge 1214. The harpoon-blade structure may be oriented in any manner relative to the taper on the sleeve 1208 at forward end 1210, as long as the sharp harpoon edge 1214 causes a severing action when drawn back into the sleeve 1208 past the edge 1210. The harpoon end 1206 also includes a tip 1216 which is used to puncture the tissue which is to be sampled, and a pocket 1202 formed behind the harpoon-type barb 1206.

Once the catheter is inserted into the urethra, the sleeve 1208 is extended from the catheter (see FIG. 5) into the urethra wall and into the prostate gland by the use of the appropriate styler sleeve tab (see FIG. 6). Then styler 1204 would be deployed into the prostate at the desired target tissue. The positioning of the harpoon tip 1206 relative to the forward end 1210 of sleeve 1208, such that upon movement of the appropriate sleeve block, the harpoon stylet 1204 moves forward of end 1210 and can be withdrawn into the opening formed by forward edge 1210 of sleeve 1208. Upon withdrawal of the harpoon styler assembly 1204 into sleeve 1208, the sharp edge 1214 will sever any tissue that expanded into pocket 1202. As the stylet 1204 is further withdrawn rearwardly into sleeve 1208, the tissue sample will be retained in the pocket 1202 of harpoon 1206 within sleeve 1208. Then, similarly to the embodiment above in conjunction with FIG. 11, the sleeve 1208 is withdrawn from the patient's body and the tissue removed from pocket 1202 for external histological examination.

Figure 13:
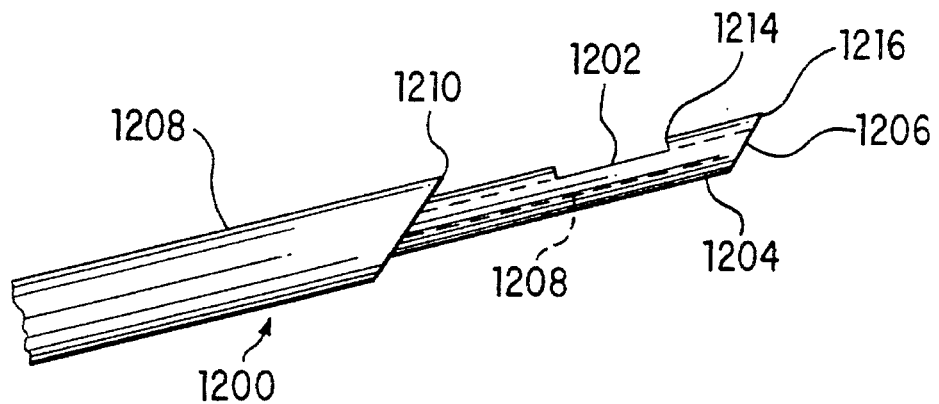
FIG. 13 is a side view of a harpoon-shaped biopsy sampling stylet.

FIG. 12 is a side view of one embodiment of this aspect of the invention with the pointed edge 1216 leading back at an angle to the cutting edge 1214. While FIG. 13 is a side view of a second embodiment of this aspect of the invention wherein the sharp edge 1216 is substantially parallel to the leading edge 1210 of sleeve 1208. However, cutting edge 1214 would operate in a similar manner as the embodiment shown in FIG. 12 to cut a sample tissue to be retained in pocket 1202.

Figure 14:
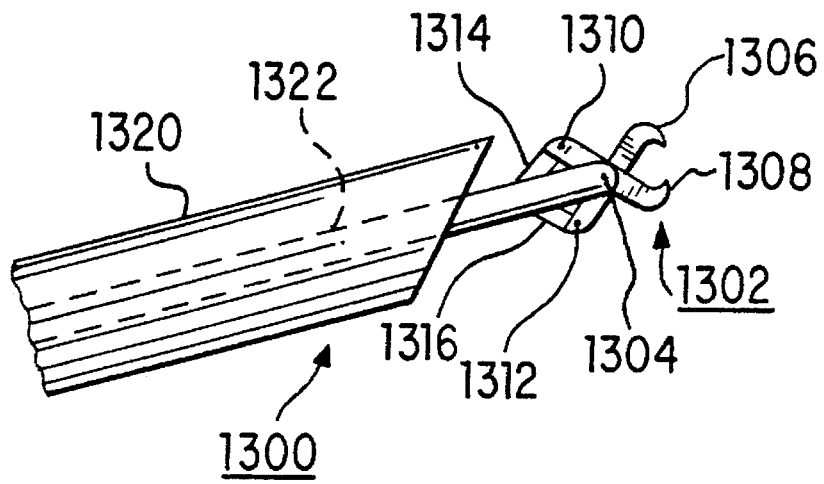
FIG. 14 is a side view of a double action biopsy jaw sampling stylet.
Figure 15:
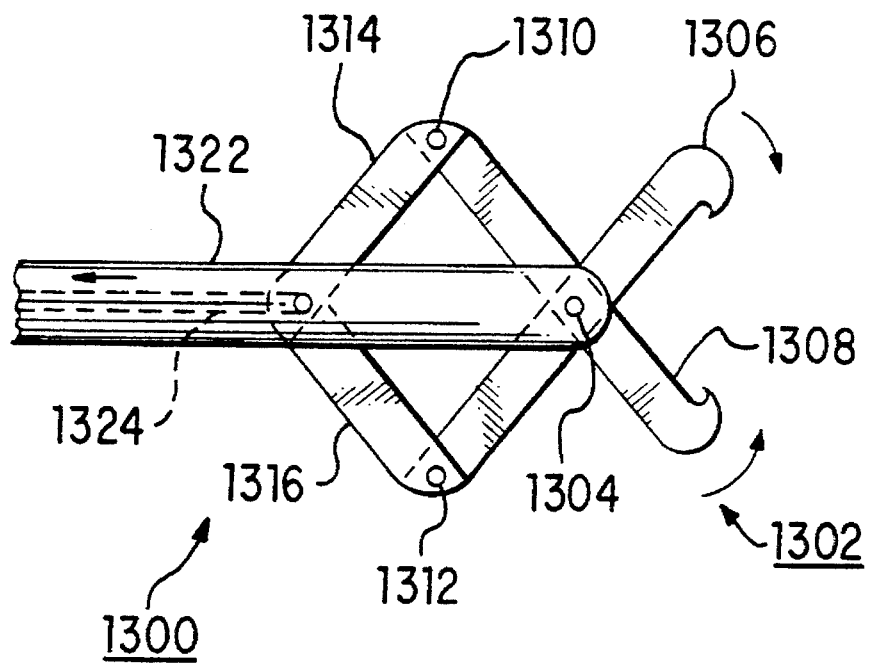
FIG. 15 is an enlarged side view of the double action jaw sampling stylet of FIG. 14.

FIGS. 14 and 15 are side, views of still another biopsy sampler stylet assembly 1300 where target tissue samples are obtained by the action of clam shell or alligator-type jaws 1302. The jaws depicted in FIG. 13 are of the double action type which include the jaws 1302 pivoted about point 1304. Comprising jaws 1302 are jaw 1306 and jaw 1308. Jaw 1306 and jaw 1308 are connected via a flexible pivot point 1302. At the forward end of each jaw 1306, 1308 would be alligator type teeth (not shown) for gripping and/or cutting the desired tissue. Alternatively, the forward ends of the jaws 1306, 1308 could be very sharp as to facilitate a cutting action upon deployment and operation of the biopsy jaws 1302.

At the other ends of both jaws 1306 and 1308 are attached arms 1316 and 1314 via pivots 1312 and 1310. Within the stylet sleeve 1320 is positioned the stylet cable 1322. Pivot point 1304 is present in the distal end of the stylet 1322 to support and operate the jaws 1302 upon deployment of the apparatus into the target tissue. When the cable 1324 is withdrawn by the operating surgeon, the arms 1314 and 1316 are pulled toward the operator which, by the double jaw action about pivot point 1304, closes jaws 1302. When jaws 1306 and 1308 come together, the sharp forward edges thereof will cut off or sever a small sample of target tissue. The stylet jaw assembly 1302 is then withdrawn into sleeve 1320, the sleeve withdraws from the tissue, and the tissue sample withdrawn and removed from the patient's body for external histological examination.

FIGS. 16 to 18 show a biopsy knife sampler stylet 1400 in combination with an RF antenna arrangement. FIG. 16 shows the stylet 1404 surrounded by sleeve 1402. Sharpened edge 1406 of the stylet 1404 aids in insertion into the selected body tissue. Wound about the central stylet 1404 is antenna wire 1408 which would be connected via antenna connector 1410 to a source of high frequency signals. If the arrangement 1400 is used as a microwave antenna as set forth in FIGS. 17 and 18, then the signals applied would be in the microwave frequency range (for example, from 915 MHz to 2.45 GHz). If the stylet arrangement 1400 is used as an RF (radio frequency) current generator to a separate body contact electrode, not shown, then the high frequency signal source would be in the range of 10 to 20 MHz.

FIG. 17 depicts an enlarged cross-sectional view B of the stylet arrangement shown in FIG. 14a. Hollow lumen 1404 is seen to be enclosed by dielectric insulating sleeve 1402. The antenna wire 1408, which is wound into the hollow lumen 1404, is shown in various positions in cross-section.

FIG. 18 is an enlarged cross-sectional representation of the embodiment of a biopsy stylet according to this invention as shown above in conjunction with FIG. 16. This stylet comprises a flexible tube 1404 having an electrode wire 1408 embedded in the surface thereof. The electrode wire is enclosed with a retractable insulating sleeve 1402. At the end of the tube 1404, a biopsy knife 1412 with a cutter tip 1412 extends through a flexible clamshell or resilient shield 1414. During advancement of the biopsy stylet, the shield 1414 is closed, and the biopsy knife 1412 is in a retracted position behind the shield. When the biopsy knife is advanced, the sharp cutter tip 1418 passes through shield and penetrates tissue with a minimum of trauma. The cutter tip 1418 has a side opening 1420 through which a sample of tissue or liquid can be aspirated through concentric suction tube 1422. Retraction of biopsy knife 1412 permits the shield 1414 to close to its initial position, shielding tissue from the sharp edge 1418.

In operation, the catheter would be inserted in the urethra in the manner set forth above. The sleeve 1402 would then be selectively deployed by the physician into the target tissue. Then the lumen 1404 with the antenna wire 1408 would be extended out from lumen 1404 into the target tissue. At this point the physician has several options. She/he could then selectively deploy the biopsy knife 1412 into the target tissue to gather sample tissue for later examination. Or the physician could ignore the biopsy knife 1412 and energize, as set forth above, the extended antenna probe 1414 to heat and thus ablate the surrounding tissue. Or the physician can operate both aspects of this embodiment in the order of the physician's choice. That is, the biopsy knife 1412 can be deployed to gather a target tissue sample. The biopsy knife could be withdrawn through the hollow lumen 1404 and out from the patient's body for external histologic examination. If the tissue contains evidence of cancer, or BPH tissue, the physician could then choose to actuate the microwave aspect of this embodiment to ablate the selected target tissue. In this embodiment choice, the hollow lumen and catheter would remain in the body while the biopsy knife arrangement 1412 is completely withdrawn for external examination. Lastly, the third option for the physician is to actuate the microwave antenna 1414 to ablate the target tissue, then deploy the biopsy knife 1412 to take a tissue sample for external examination and review. This embodiment is particularly advantageous to the physician and the patent, as the detection, examination, and ablation of the selected tissue can occur with only one insertion of the catheter and stylet arrangement.

While the invention has been described with reference to specific preferred embodiments, it will be understood by those skilled in the art that various changes may be made and equivalents may be substituted for elements thereof without departing from the true spirit and scope of the invention. In addition, many modifications may be made without departing from the essential teachings of the invention.

What is claimed is:

1. A medical probe comprising a catheter having at least two stylet ports toward the distal end thereof, at least two flexible stylets disposed within the catheter and having sharp distal tips for puncturing tissue, means for advancing the stylets outward through the stylet ports and through intervening tissue to target tissue, means for energizing the stylets to apply ablating power to the target tissue, and means carried by the stylets for cutting and collecting a sample of the target tissue.

2. The medical probe of claim 1 including non-conductive sleeves movable longitudinally of the stylets to expose selected portions of the stylets to the target tissue.

3. A medical probe apparatus comprising a catheter having a stylet port toward the distal end thereof, a flexible stylet disposed within the catheter and having a sharp distal tip for puncturing tissue, means for advancing the stylet outward through the stylet port and through intervening tissue to target tissue, means for energizing the stylet to apply ablating power to the target tissue, and means carried by the stylet for cutting and collecting a sample of the target tissue.

4. The medical probe apparatus of claim 3 wherein the means for energizing the stylet includes means for applying microwave energy to the target tissue.

5. The medical probe apparatus of claim 3 wherein the stylet is enclosed within a non-conductive sleeve, the stylet and sleeve being movable longitudinally of each other to expose a selected portion of the stylet in the target tissue.

6. A medical probe apparatus comprising a catheter having a stylet port toward the distal end thereof, a flexible stylet disposed within the catheter and having a sharp distal end for puncturing tissue, means for advancing the stylet outward through the stylet port and through intervening tissue to target tissue, and means near the distal end of the stylet for cutting and collecting a sample of the target tissue.

7. The medical probe apparatus of claim 6 wherein the means for cutting and collecting a sample of the target tissue includes a cutting edge which faces away from the distal end of the stylet.

8. The medical probe apparatus of claim 7 further including a sleeve which surrounds the stylet and is longitudinally extensible and retractable relative to the stylet, the sleeve having a sharpened distal end which cooperates with the cutting edge of the stylet in cutting the target tissue as the stylet is retracted relative to the sleeve.

9. The medical probe apparatus of claim 7 wherein the means for cutting and collecting a sample of the target tissue comprises a biopsy needle.

10. The medical probe apparatus of claim 7 wherein the means for cutting and collecting a sample of the target tissue comprises a clam shell or jaw stylet.

11. The medical probe apparatus of claim 3 wherein the means for cutting and collecting a sample of the target tissue includes a cutting edge which faces rearwardly from the distal end of the stylet.

12. The medical probe apparatus of claim 11 wherein the means for cutting and collecting a sample of the target tissue comprises a biopsy needle.

13. The medical probe apparatus of claim 1 wherein the means for cutting and collecting a sample of the target tissue includes a cutting edge which faces rearwardly from the distal end of the stylet.

14. The medical probe apparatus of claim 11 wherein the means for cutting and collecting a sample of the target tissue comprises a clam shell or alligator tooth apparatus.

15. The medical probe apparatus of claim 11 wherein the means for cutting and collecting a sample of the target tissue comprises a core sampling apparatus.

16. The medical probe apparatus of claim 11 wherein the means for cutting and collecting a sample of the target tissue comprises a hollow tube having a sharpened end for facilitating penetration into the tissue and collection of the sample.

17. The medical probe apparatus of claim 7 wherein the stylet is enclosed within an insulating sleeve which is longitudinally movable relative to the stylet to expose a selected portion of the stylet to the target tissue, and the stylet comprises a hollow tube having an aperture along the lateral side thereof toward the distal end of said tube, together with means for applying a negative pressure to the hollow tube to draw a tissue sample into the tube through the aperture.

18. The medical apparatus claim 17 wherein the cutting edge is positioned at one end of the aperture, and the insulating sleeve has a sharpened tip end which cooperates with the cutting edge of the tube to cut the sample from the target tissue as the tube is withdrawn into the sleeve.

19. The medical probe apparatus of claim 7 wherein means for cutting and collecting a sample of the target tissue comprises a clam shell or alligator tooth apparatus.

20. The medical probe apparatus of claim 7 wherein the stylet is enclosed within an insulating sleeve, the stylet and the sleeve being movable longitudinally of each other to expose a selected portion of the stylet surface, the means for cutting and collecting a sample of the target tissue comprises a clam shell or alligator tooth biopsy device which is opened when [deployed by the longitudinal movement of the stylus is extended longitudinally relative to the sleeve and closed when the stylet is withdrawn relative to the insulating sleeve.

21. The medical probe apparatus of claim 7 wherein the stylet is enclosed within an insulating sleeve, the stylet and the sleeve being movable longitudinally of each other to expose a selected portion of the stylet, and the means for cutting and collecting a sample of the target tissue comprises a hollow tube having a sharp, barbed distal end for cutting and gathering the sample.

22. The medical probe apparatus of claim 17 further including means for energizing the stylet to apply ablating power to the target tissue.

23. The medical probe apparatus of claim 22 including an antenna wire curled around the insulating sleeve from the proximal end to the distal end of said sleeve, and electromagnetic antenna means coupled to the antenna wire and capable of being deployed from the insulating sleeve.

* * * * *